(12) United States Patent
Johnson

(10) Patent No.: US 7,829,690 B2
(45) Date of Patent: Nov. 9, 2010

(54) **REGULATORY DNA ELEMENTS FROM *AGROBACTERIUM VITIS* S4**

(75) Inventor: Susan J. Johnson, New London, CT (US)

(73) Assignee: Monsanto Technology LLC, St. Louis, MO (US)

( * ) Notice: Subject to any disclaimer, the term of this patent is extended or adjusted under 35 U.S.C. 154(b) by 650 days.

(21) Appl. No.: 11/747,432

(22) Filed: May 11, 2007

(65) Prior Publication Data

US 2007/0271635 A1 Nov. 22, 2007

Related U.S. Application Data

(60) Provisional application No. 60/801,333, filed on May 18, 2006.

(51) Int. Cl.
*C07H 21/04* (2006.01)
*C12N 15/82* (2006.01)

(52) U.S. Cl. .................. 536/24.1; 435/320.1; 435/419; 435/468

(58) Field of Classification Search ........................ None
See application file for complete search history.

(56) References Cited

PUBLICATIONS

Canaday et al., Mol. Gen. Genet., 1992, vol. 235, pp. 292-203.*
Otten et al., Mol. Gen. Genet., 1994, vol. 245, pp. 493-505.*
Genes, Third Ed., Benjamin Lewin, Ed., John Wily & Sons, Publ., New York, 1987, p. 728.*
Benfey et al., "The CaMV 35S enhancer contains at least two domains which can confer different developmental and tissue-specific expression patterns," *EMBO J.*, 8(8):2195-2202, 1989.
Cho et al., "Regulation of root hair initiation and expansin gene expression in arabidopsis," *The Plant Cell*, 14:3237-3253, 2002.
GenBank Accession No. M91608, dated Sep. 23, 1994.
GenBank Accession No. NC_003065, dated Jul. 21, 2008.
Kim et al., "A 20 nucleotide upstream element is essential for the nopaline synthase (nos) promoter activity," *Plant Molecular Biology*, 24:105-117, 1994.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Welsch et al., "Structural and functional characterization of the phytoene synthase promoter from arabidopsis thaliana," *Planta*, 216:523-534, 2003.

* cited by examiner

*Primary Examiner*—Ashwin Mehta
(74) *Attorney, Agent, or Firm*—Erin C. Robert, Esq.; Sonnenschein Nath & Rosenthal LLP

(57) ABSTRACT

Non-coding regulatory element polynucleotide molecules isolated from a nopaline synthase gene and vitopine synthase gene of *Agrobacterium vitis* are useful for expressing transgenes in plants.

12 Claims, No Drawings

SEQUENCE LISTING

<160> NUMBER OF SEQ ID NOS: 6

<210> SEQ ID NO 1
<211> LENGTH: 500
<212> TYPE: DNA

-continued

<213> ORGANISM: Agrobacterium vitis S4

<400> SEQUENCE: 1

| | | | | | |
|---|---|---|---|---|---|
| acccgtgttc | accgctctga | ggcttgcgaa | ctctcagctc | cgagtgctga | ccgcccttcc | 60 |
| aatggatcgt | gagcaccacg | tcgcgcaccg | catcgtcaac | agcttagata | catgcaaact | 120 |
| attatatgaa | tgcacgaatt | aacgaacatg | acataacgat | aaatcctgtc | atacgtcact | 180 |
| gcttacagcc | aaataacgta | acggtaaacg | tgcgtaggcg | cttacgtaca | tctaagcacc | 240 |
| taacccgtaa | tgataggtag | ttaaggacgc | cgcgtgtcca | acatcgcttt | ctcgggtcca | 300 |
| ttttttcatc | aactgcgctc | agcagataaa | taattgaagg | catgaaattc | aagcttccta | 360 |
| cgtacgcagt | gacctatcta | tccgagaaat | tcaacacagc | tgtgctggca | acttgaaggg | 420 |
| acccacccc | cttctcccta | tttaagggcc | aaagaacgag | ggaaccctca | cctcaaaact | 480 |
| tcttcaaaac | caatctcaca | | | | | 500 |

<210> SEQ ID NO 2
<211> LENGTH: 26
<212> TYPE: DNA
<213> ORGANISM: Agrobacterium vitis S4

<400> SEQUENCE: 2
taaacgtgcg taggcgctta cgtaca            26

<210> SEQ ID NO 3
<211> LENGTH: 300
<212> TYPE: DNA
<213> ORGANISM: Agrobacterium vitis S4

<400> SEQUENCE: 3

| | | | | | |
|---|---|---|---|---|---|
| aacccgtctt | ccagcttgat | ctgatgtaat | atattatgat | gcactgaagc | atccagcgtg | 60 |
| tgtttttatt | tcttgtcttg | tgagaggctt | gaataaggtc | tggcatgccc | ggcgccactg | 120 |
| tataatatgt | gatattgtaa | aatatgctgt | atttccttag | ttgaaattca | cggaaaaatt | 180 |
| tgttttaaa | taacttaaaa | aataaataaa | cgaaaaaata | caccaacaat | cgatattaat | 240 |
| gcttctaaat | ttcacttagc | gcgaataaat | atcagatacg | ccaacaagaa | cataataacg | 300 |

<210> SEQ ID NO 4
<211> LENGTH: 500
<212> TYPE: DNA
<213> ORGANISM: Agrobacterium vitis S4

<400> SEQUENCE: 4

| | | | | | |
|---|---|---|---|---|---|
| tatttcttta | ttttttaaa | aatctaatat | ataaatataa | tatcactgcc | gataatgtta | 60 |
| ctattataac | atttatttct | aggctcacca | atattgataa | agtaatctta | atcgttattc | 120 |
| taggtcaata | ataaaattgt | gatccgtta | catattcaat | cccatgcttt | gagcttgata | 180 |
| atccgcattt | tacggtggag | agcatcttgt | acgacgcggc | atatgatcta | attgcattct | 240 |
| ggaaataaca | gcatgaatat | tgctatgcgt | aactttcgtg | ccactcaagc | gaatgcactt | 300 |
| tattcgttac | tttcaaatta | tttaacgaat | attattaacg | tgatacgtgt | aaatttcttt | 360 |
| atcattgctt | tgattgctgt | ctggaggatg | ttgtttgctt | aagcccgagg | ggaagcgcct | 420 |
| ctataaatga | gcttggaaga | accttctctc | cactgcaatc | aactaagcat | tacattgcat | 480 |
| tccaataaaa | tacttaaaca | | | | | 500 |

<210> SEQ ID NO 5
<211> LENGTH: 27

```
-continued

<212> TYPE: DNA
<213> ORGANISM: Agrobacterium vitis S4

<400> SEQUENCE: 5
catcttgtac gacgcggcat atgatct                                               27

<210> SEQ ID NO 6
<211> LENGTH: 300
<212> TYPE: DNA
<213> ORGANISM: Agrobacterium vitis S4

<400> SEQUENCE: 6
tatcggacat ccgttgcaaa aatccaaaaa atacatatga tgccatattt ataaaatttt           60
aataaacggc agggcgctca tgtgaagcga atgcctttgt attgtgtgca acgttttcat          120
ttttatggtg tgtaataaat catacttata ttgcgtgtgc attgctgcaa ggttcccatg          180
ttaaatattt gcgcttggta ttcctgggaa ataatataaa tttattttca atacataacc          240
ttcacaccac agagttacta gcttttttaac aaacaaaatt aacaataaac tcaattgcta         300
```

REGULATORY DNA ELEMENTS FROM *AGROBACTERIUM VITIS* S4

This application claims benefit under 35 USC §119(e) of U.S. provisional application Ser. No. 60/801,333 filed 18 May 2006, herein incorporated by reference in its entirety.

This invention was made with Government support under Grant No. EF-0333297 awarded by the U.S. National Science Foundation. The Government has certain rights in the invention.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01178.rpt, which is 2,960 bytes (measured in MS-DOS) and was created on May 17, 2006, all of which are incorporated herein by reference.

FIELD OF THE INVENTION

Disclosed herein are recombinant DNA constructs comprising promoter elements and polyadenylation elements from vitopine synthase and nopaline synthase genes from *Agrobacterium vitis* and methods of making and using such constructs in transgenic plant cells, plants and seeds.

SUMMARY OF THE INVENTION

This invention provides recombinant DNA constructs for regulating the expression of a gene in a plant cell comprising a transcription promoter element or polyadenylation element derived from a vitopine synthase or nopaline synthase gene of *Agrobacterium vitis* operably linked to DNA of said gene. In one aspect of the invention the transcription promoter element can comprise a promoter from a vitopine synthase or nopaline synthase gene from *A. vitis*, a promoter enhancer from said genes or both a promoter and a promoter enhancer from said gene, Embodiments of the invention includes transgenic plant cells, transgenic plants and transgenic seeds stably transformed with such, the recombinant constructs. Genes in plant cells can be regulated by using such a transcription promoter to transcribe DNA encoding a protein to be expressed in a cell lined to such a polyadenylation element. Alternatively, genes in a plant cell can be regulated by using a promoter element to transcribe RNA for gene suppression of a gene, e.g. double-stranded RNA targeted to a native plant gene to be suppressed.

The useful elements of this invention specifically include a transcription promoter from an *A. vitis* vitopine synthase gene having nucleotides of SEQ ID NO:1, a transcription promoter from an *A. vitis* nopaline synthase gene having nucleotides of SEQ ID NO:4, a transcription promoter comprising a transcription enhancer from an *A. vitis* vitopine synthase gene having nucleotides of SEQ ID NO:2, a transcription promoter comprising a transcription enhancer from an *A. vitis* nopaline synthase gene having nucleotides of SEQ ID NO:5, a polyadenylation element from an *A. vitis* vitopine synthase gene having nucleotides of SEQ ID NO:3, and a polyadenylation element from an *A. vitis* nopaline synthase gene having nucleotides of SEQ ID NO:6.

Particularly claimed in this invention are regulatory elements identified from *Agrobacterium vitis* that function in the transcriptional control of nopaline synthase or vitopine synthase genes. Preferably, such regulatory elements selected from the group consisting of SEQ ID NO:1 through SEQ ID NO:6 are claimed.

DETAILED DESCRIPTION OF THE INVENTION

The non-coding regulatory elements from the vitopine and nopaline synthase genes of *Agrobacterium vitis* S4 were identified in a project to sequence the genome of *A. vitis*. Known opine synthase gene sequences from several different *Agrobacterium* species were identified from a public database (GenBank), and were selected using BLAST against the *Agrobacterium vitis* S4 genome. These gene sequences were selected due to their demonstrated utility of expression of transgenes in plants. Protein sequences identified from the BLAST search were clearly related to known opine synthase proteins. The sequences which were found to share significant percent identity with sequences mined from the *A. vitis* genome sequencing effort included the vitopine synthase sequence of *A. vitis* strain S4 and a nopaline synthase homolog from *A. tumefaciens* strain C58. The protein sequences for vitopine synthase (*Agrobacterium vitis*) and octopine synthase (*Agrobacterium tumefaciens*) share 67% identity. Protein sequences from the other *Agrobacterium vitis* opine synthesis gene (nopaline synthase homolog) and nopaline synthase (*Agrobacterium tumefaciens*) share 43% identity.

Each putative *A. vitis* S4 gene was aligned with its corresponding target BLAST hit. The putative promoter and terminator regions of the query *A. vitis* S4 sequences were aligned with and assessed for percent sequence identity with the public database *A. vitis* S4 vitopine synthase DNA sequences flanking the known coding regions of the target sequences upstream and downstream, The putative promoter and terminator regions of the query *A. vitis* S4 sequences were aligned with and assessed for percent sequence identity with the public database *A. tumefaciens* nopaline synthase homolog DNA sequences flanking the known coding regions of the target sequences upstream and downstream, respectively.

These genes were matched against known replicons identified from the *A. vitis* sequencing effort, and analyzed for the presence of T-DNA borders using the method of Gerard et al. (Plasmid 28: 146-156, 1992). Both the putative vitopine synthase gene and the putative nopaline synthase homolog mapped to regions on the 259 kb plasmid of *A. vitis* S4 (pTiS4).

As used herein, the term "fragment" refers to a DNA molecule with that comprises a functional number of contiguous nucleotides bases defined by SEQ ID NO:1-6, e.g. a segment of SEQ ID NO:1 and 4 comprising at least a TATA box or a segment of SEQ ID NO:3 and 6 comprising at least a polyadenylation site or signal or splice site.

The regulatory elements useful in the various aspects of this invention include elements having minor nucleotide modification from SEQ ID NO:1 through 6, i.e. comprising a fragment of contiguous nucleotides with at least 90% identity to contiguous nucleotides of a substantial fragment (at least ½ the length, more preferably at least 80% of the length or more up to 100% of the full length) of any of SEQ ID NO:1 through 6, more preferably 95% or more, e.g. 98% or even 100% identity.

The recombinant DNA constructs of the invention can be assembled on a plasmid to facilitate *Agrobacterium*-mediated plant transformation. Such plasmids typically are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permit the integration of the T-DNA into the genome of a plant cell (see for example U.S. Pat. No. 6,603,061, herein incorporated by reference in its entirety). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene.

Method for Preparing Transformed Cells

The recombinant DNA constructs of this invention are useful for preparing transgenic plant cells. Numerous methods for transforming plant cells with recombinant DNA are known in the art and may be used in the present invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. No. 6,194,636 and U.S. Pat. No. 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are regenerated from about 6 weeks to 10 months after a transformant is identified, depending on the initial tissue. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or enhanced water deficit tolerance or both.

Not all transgenic events will provide transgenic plant seed of this invention depending on factors, such as location and integrity of the recombinant DNA, copy number, unintended insertion of other DNA, etc. As a result transgenic plants for producing seeds of this invention are identified by screening transformed plants or progeny seed for enhanced trait, e.g., water stress tolerance. For efficiency a screening program is designed to evaluate multiple transgenic plants (events) comprising the recombinant DNA, e.g., multiple plants from 2 to 20 or more transgenic events.

Having now generally described the invention, the same will be more readily understood through reference to the following examples which are provided by way of illustration, and are not intended to be limiting of the present invention, unless specified. Each patent reference cited herein is herein incorporated by reference in its entirety. The following examples are included to illustrate aspects and embodiments of the invention.

Example 1

This example illustrates the cloning of the regulatory elements from *A. vitus*, preparation of recombinant DNA constructs and plasmids, plant cell transformation and plants PCR amplification of non-coding regulatory sequences, cloning into vectors, transformation into plant cells, and functional screening in an expression assay The non-coding regulatory elements with a DNA strand of SEQ ID NO:1 through SEQ ID NO:6 are amplified by PCR from *A. vitis* genomic DNA and cloned into an expression vector containing a reporter transgene.

Specifically a first recombinant DNA construct is fabricated with a promoter element with a DNA strand of SEQ ID NO:1 operably linked to DNA encoding an nptII marker followed by a polyadenylation element with a DNA strand of SEQ ID NO:3. The construct is inserted into a first plasmid for Agrobacterium-mediated transformation. The plasmid is used to transform corn cells and transgenic corn cells are selected as having kanamycin resistance.

A second recombinant DNA construct is fabricated essentially like the first recombinant DNA construct with the further addition of a promoter enhancer element with a DNA strand of SEQ ID NO:2 following the promoter element. The construct is inserted into a plasmid and transformed into corn cells and transgenic corn cells are selected as having kanamycin resistance.

A third recombinant DNA construct is fabricated with a promoter element with a DNA strand of SEQ ID NO:4 operably linked to DNA encoding a glyphosate-resistant EPSPS gene followed by a polyadenylation element with a DNA strand of SEQ ID NO:6. The construct is inserted into the first plasmid containing the first recombinant DNA construct. The plasmid is used to transform corn cells and transgenic cells are selected as having kanamycin resistance. Transgenic cells are regenerated into plants which exhibit resistance to glyphosate herbicide.

A fourth recombinant DNA construct is fabricated with a promoter element having a DNA strand of SEQ ID NO:4 and promoter enhancer element with a DNA strand of SEQ ID NO:5 operably linked to DNA encoding an EPSPS gene followed by a polyadenylation element with a DNA strand of SEQ ID NO:6. The construct is inserted into a plasmid containing the first recombinant DNA construct. The plasmid is used to transform corn cells and transgenic cells are selected as having kanamycin resistance. Transgenic cells are regenerated into plants which exhibit resistance to glyphosate herbicide. The plants are self-pollinated producing segregating homozygous, heterozygous and null seeds, which are planted to produce plants which are analyzed for zygosity of the recombinant DNA. The homozygous plants are self-pollinated to produce seed which are homozygous for the recombinant DNA.

A fifth recombinant DNA construct is fabricated comprising a promoter element with a DNA strand of SEQ ID NO:4 and a promoter enhancer element with a DNA strand of SEQ ID NO:5 operably linked to sense and anti-sense DNA from the coding sequence of a GUS gene followed by a polyadenylation element with a DNA strand of SEQ ID NO:6. The construct is inserted into a plasmid containing the first recombinant DNA construct. The plasmid is used to further transform transgenic corn cells derived from a corn plant having homozygous recombinant DNA encoding the GUS marker; transgenic cells are selected as having kanamycin resistance. Transgenic cells are regenerated into plants in which the GUS gene is suppressed.

Having illustrated and described the principles of the present invention, it should be apparent to persons skilled in the art that the invention can be modified in arrangement and detail without departing from such principles. We claim all modifications that are within the spirit and scope of the appended claims. All patent references cited are herein incorporated by reference.

I claim:

1. A polynucleotide molecule that functions in the transcriptional regulation of a gene encoding nopaline synthase, the polynucleotide molecule comprising a sequence selected from the group consisting of:
   (a) the nucleic acid sequence of SEQ ID NO:4 or SEQ ID NO: 5,
   (b) a nucleic acid sequence with at least 95% identity to SEQ ID NO:4 or SEQ ID NO:5; and
   (c) a fragment of the nucleic acid sequence of SEQ ID NO:4 or SEQ ID NO:5,
   wherein the polynucleotide molecule is operably linked to a transgene.

2. The polynucleotide molecule of claim 1, wherein said molecule comprises a promoter.

3. The polynucleotide molecule of claim 1, wherein said molecule comprises an enhancer.

4. A recombinant polynucleotide construct for regulating the expression of a transgene in a plant cell comprising the polynucleotide molecule of claim 1 and a polyadenylation element operably linked to DNA of said transgene.

5. The recombinant polynucleotide construct of claim 4 wherein said polynucleotide molecule comprises an enhancer.

6. A transgenic plant cell stably transformed with the polynucleotide molecule of claim 1.

7. A transgenic plant stably transformed with the polynucleotide molecule of claim 1.

8. A seed comprising the polynucleotide molecule of claim 1.

9. The polynucleotide molecule of claim 1, comprising the nucleic acid sequence of SEQ ID NO:4 or SEQ ID NO:5.

10. The polynucleotide molecule of claim 1, comprising a nucleic acid sequence with at least 95% identity to SEQ ID NO:4 or SEQ ID NO:5.

11. The polynucleotide molecule of claim 1, comprising a fragment of the nucleic acid sequence of SEQ ID NO:4 or SEQ ID NO:5.

12. The recombinant polynucleotide construct of claim 4, wherein the transgene encodes a protein.

* * * * *